United States Patent
Shinkawa et al.

(10) Patent No.: US 11,213,070 B2
(45) Date of Patent: Jan. 4, 2022

(54) FLAVOR SOURCE UNIT AND FLAVOR INHALER

(71) Applicant: JAPAN TOBACCO INC., Tokyo (JP)

(72) Inventors: Takeshi Shinkawa, Tokyo (JP); Takeshi Akiyama, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 57 days.

(21) Appl. No.: 16/694,603

(22) Filed: Nov. 25, 2019

(65) Prior Publication Data

US 2020/0085098 A1 Mar. 19, 2020

Related U.S. Application Data

(63) Continuation of application No. PCT/JP2018/016948, filed on Apr. 26, 2018.

(30) Foreign Application Priority Data

May 26, 2017 (JP) .............................. JP2017-104173

(51) Int. Cl.
*A24F 40/20* (2020.01)
*H05B 1/02* (2006.01)
(Continued)

(52) U.S. Cl.
CPC .............. *A24F 40/20* (2020.01); *A24D 1/20* (2020.01); *A24F 40/42* (2020.01); *H05B 1/0297* (2013.01); *H05B 3/46* (2013.01); *A24F 40/46* (2020.01)

(58) Field of Classification Search
CPC ...................................................... A24F 40/20
See application file for complete search history.

(56) References Cited

U.S. PATENT DOCUMENTS

| | | | |
|---|---|---|---|
| 4,186,756 A | * | 2/1980 | Takemoto .............. A24B 15/14 131/355 |
| 4,765,348 A | | 8/1988 | Honeycutt |

(Continued)

FOREIGN PATENT DOCUMENTS

| | | |
|---|---|---|
| EA | 030672 B1 | 9/2018 |
| EA | 032720 B1 | 7/2019 |

(Continued)

OTHER PUBLICATIONS

International Search Report (PCT/ISA/210), issued in PCT/JP2018/016948, dated Jul. 31, 2018.

(Continued)

*Primary Examiner* — James Harvey
(74) *Attorney, Agent, or Firm* — Birch, Stewart, Kolasch & Birch, LLP

(57) ABSTRACT

A columnar lump body includes a first lump body end face that forms an air inflow end, a second lump body end face that forms an air outflow end, and a lump body side face that continues into an outer periphery of the first lump body end face and an outer periphery of the second lump body end face. The columnar lump body is disposed in such a way as to block an inside space of the cylindrical body side wall by the lump body side face contacting any portion of an inner surface of the cylindrical body side wall. A first space is provided at least either between the first cylindrical body end face and the first lump body end face or between the second cylindrical body end face and the second lump body end face.

22 Claims, 12 Drawing Sheets

(51) Int. Cl.
    *H05B 3/46*     (2006.01)
    *A24F 40/42*     (2020.01)
    *A24D 1/20*     (2020.01)
    *A24F 40/46*     (2020.01)

(56) References Cited

U.S. PATENT DOCUMENTS

| | | | |
|---|---|---|---|
| 4,967,774 A | 11/1990 | White | |
| 9,682,204 B2 * | 6/2017 | Matsumoto | B65B 1/20 |
| 2003/0159703 A1 | 8/2003 | Yang et al. | |
| 2007/0240729 A1 | 10/2007 | Moffitt | |
| 2014/0069444 A1 * | 3/2014 | Cyphert | A24F 1/00 |
| | | | 131/194 |
| 2015/0013696 A1 * | 1/2015 | Plojoux | A61M 15/06 |
| | | | 131/328 |
| 2015/0374037 A1 | 12/2015 | Akiyama et al. | |
| 2017/0238605 A1 * | 8/2017 | Matsumoto | A24F 40/485 |
| 2017/0238608 A1 | 8/2017 | Matsumoto et al. | |
| 2018/0325163 A1 * | 11/2018 | Ichitsubo | A24B 15/287 |
| 2020/0085098 A1 * | 3/2020 | Shinkawa | A61M 15/06 |

FOREIGN PATENT DOCUMENTS

| | | |
|---|---|---|
| EP | 0 311 581 A1 | 4/1989 |
| JP | 11-164679 A | 6/1999 |
| JP | 2000-41654 A | 2/2000 |
| JP | 2005-518204 A | 6/2005 |
| JP | 2016-185158 A | 10/2016 |
| WO | WO 2015/179388 A1 | 11/2015 |
| WO | WO 2016/075749 A1 | 5/2016 |

OTHER PUBLICATIONS

Eurasian Office Action for Eurasian Application No. 201992791/31, dated Oct. 13, 2020, with an English translation.
Japanese Notice of Reasons for Refusal for Japanese Application No. 2019-519534, dated Dec. 10, 2020, with an English translation.
Extended European Search Report for European Application No. 18806198.0, dated Jan. 28, 2021.

* cited by examiner

UPSTREAM ←PREDETERMINED DIRECTION A→ DOWNSTREAM

FLAVOR SOURCE UNIT AND FLAVOR INHALER

CROSS REFERENCE TO RELATED APPLICATIONS

The present application is a continuation application of International Application No. PCT/W2018/016948, filed on Apr. 26, 2018, which claims priority under 35 U.S.C. 119(a) to Patent Application No. 2017-104173, filed on May 26, 2017, all of which are hereby expressly incorporated by reference into the present application.

TECHNICAL FIELD

The invention relates to a flavor source unit and a flavor inhaler.

BACKGROUND ART

A flavor inhaler with a flavor source unit has been known. The flavor source unit includes a cylindrical body containing a plurality of flavor pieces, and a pair of end walls having air permeability. The end walls are each disposed in an end portion of the cylindrical body. For example, a space demarcated by the end walls and the cylindrical body is filled with the flavor pieces at a filling rate of 95 percent or higher.

CITATION LIST

Patent Literature

PTL 1: International Patent Publication No. WO 2015-179388

SUMMARY OF INVENTION

A first characteristic is a flavor source unit comprising a columnar lump body that is formed of a plurality of flavor pieces, and a cylindrical body containing the columnar lump body; the cylindrical body including a first cylindrical body end face that forms an air inflow end, a second cylindrical body end face that forms an air outflow end, and a cylindrical body side wall connecting an outer periphery of the first cylindrical body end face and an outer periphery of the second cylindrical body end face; the columnar lump body including a first lump body end face that forms an air inflow end, a second lump body end face that forms an air outflow end, and a lump body side face that continues into an outer periphery of the first lump body end face and an outer periphery of the second lump body end face; the columnar lump body being disposed in such a way as to block an inside space of the cylindrical body side wall by the lump body side face contacting any portion of an inner surface of the cylindrical body side wall, wherein a first space is provided at least either between the first cylindrical body end face and the first lump body end face or between the second cylindrical body end face and the second lump body end face.

A second characteristic according to the first characteristic is that the flavor source unit comprises a first end wall which demarcates the inside space of the cylindrical body side wall on a side close to the first cylindrical body end face, and a second end wall which demarcates the inside space of the cylindrical body side wall on a side close to the second cylindrical body end face, and that a second space forming a portion of the first space is provided at least either between the first end wall and the first lump body end face or between the second end wall and the second lump body end face.

A third characteristic according to the second characteristic is that the first end wall or the second end wall, whichever wall body faces the second space, comprises a filter.

A fourth characteristic according to any one of the first to third characteristics is that the lump body side face is fixed to the inner surface of the cylindrical body side wall.

A fifth characteristic according to the second characteristic or the third or fourth characteristic referring to the second characteristic is that the first end wall and the first lump body end face are in contact, and the second space is provided between the second end wall and the second lump body end face.

A sixth characteristic according to any one of the first to fifth characteristics is that the cylindrical body includes a connect portion which is mechanically connected to a body of a flavor inhaler, and that the first space is adjacent to the connect portion.

A seventh characteristic according to any one of the second characteristic and the third to sixth characteristics referring to the second characteristic is that the second space has a volume of 5 to 90 percent of a capacity of a space surrounded by the first end wall, the second end wall, and the cylindrical body side wall.

An eighth characteristic according to any one of the first to seventh characteristics is that the first cylindrical body end face is the same shape and size as the second cylindrical body end face.

A ninth characteristic according to any one of the first to eighth characteristics is that the first lump body end face is the same shape and size as the second lump body end face.

A tenth characteristic according to the first characteristic is that the flavor source unit comprises a first end wall which demarcates the inside space of the cylindrical body side wall on a side close to the first cylindrical body end face, and a second end wall which demarcates the inside space of the cylindrical body side wall on a side close to the second cylindrical body end face, and that at least either one of the first end wall and the second end wall fills in the first space in such a manner as to contact the columnar lump body.

An eleventh characteristic according to any one of the first to tenth characteristics is that the columnar lump body is a compressed body formed of the plurality of flavor pieces.

A twelfth characteristic according to any one of the first to eleventh characteristics is that the plurality of flavor pieces includes at least either an aroma chemical or a binder.

A thirteenth characteristic according to any one of the first to twelfth characteristics is that the columnar lump body has a bulk density of 130 to 160 percent of a loose bulk density of the plurality of flavor pieces.

A fourteenth characteristic according to any one of the first to thirteenth characteristics is that the columnar lump body has a bulk density higher than a tight bulk density of the plurality of flavor pieces.

A fifteenth characteristic according to any one of the first to fourteenth characteristics is that the plurality of flavor pieces has a compression degree ranging from 22 to 34 percent, inclusive.

A sixteenth characteristic according to any one of the first to fifteenth characteristics is that the plurality of flavor pieces has a loose bulk density ranging from 0.40 to 0.54 g/cm$^3$, inclusive.

A seventeenth characteristic according to any one of the first to fifteenth characteristics is that the plurality of flavor pieces has a tight bulk density ranging from 0.68 to 0.71 g/cm$^3$, inclusive.

An eighteenth characteristic according to any one of the first to seventeenth characteristics is that each of the plurality of flavor pieces has a size ranging from 0.2 to 1.4 mm, inclusive.

A nineteenth characteristic is a flavor inhaler comprising the flavor source unit as described in any one of the first to eighteenth characteristics.

A twentieth characteristic according to the nineteenth characteristic is that the flavor inhaler includes a body that holds the flavor source unit in a detachable manner.

A twenty-first characteristic according to the nineteenth or twentieth characteristic is that the flavor inhaler includes an atomization unit located further upstream than the flavor source unit.

A twenty-second characteristic according to any one of the nineteenth to twenty-first characteristics is that the flavor source unit includes a mouthpiece to be held in a user's mouth.

DESCRIPTION OF EMBODIMENTS

Figure 1:
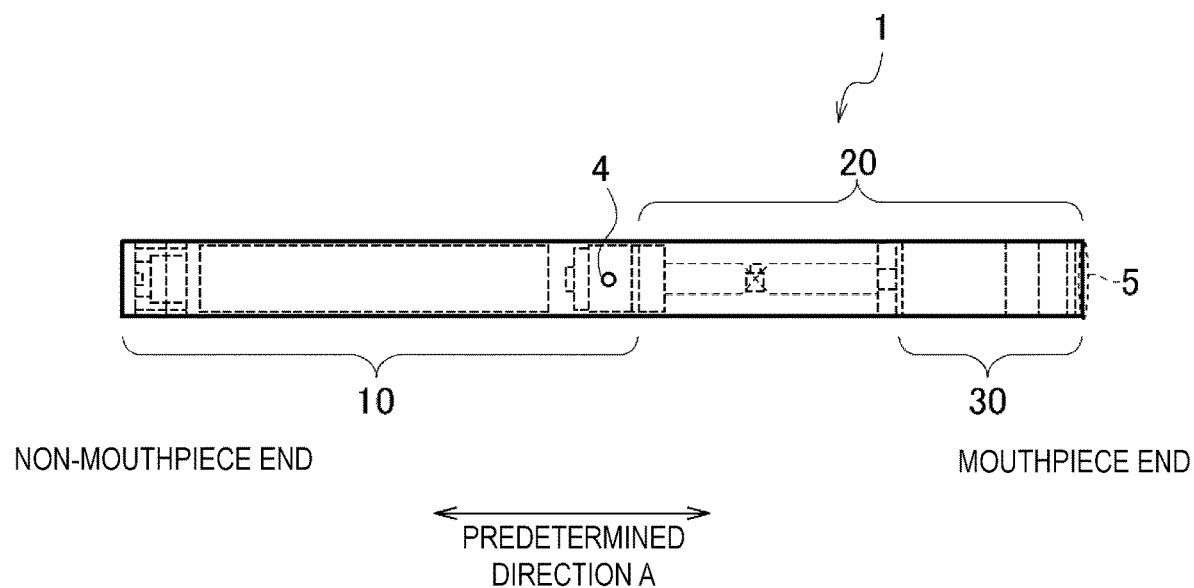
FIG. 1 is a sectional view of a non-burning flavor inhaler 1 according to an embodiment.

Embodiments will be described below. In the following description of the attached drawings, identical or similar components will be provided with identical or similar reference signs. It should be noted that the drawings are schematic diagrams, and therefore, that a dimension ratio might differ from the actual one.

Specific dimensions and the like therefore should be estimated with reference to the following description. Needless to say, the drawings also might include the components different from one another in dimension relation and ratio.

Summary of Disclosure

According to the flavor source unit described in the BACKGROUND ART, the filling rate of the plurality of flavor pieces is 95 percent or higher. If the amount of the plurality of flavor pieces may be small, the flavor source unit needs to be downsized to achieve the filling rate of 95 percent or higher. Considering the ease of production and handling of the flavor source unit, however, it is not preferable that the flavor source unit is excessively downsized.

On the other hand, if the filling rate of 95 percent or higher is failed to be achieved, there is a possibility that the air inhaled by the user does not uniformly contact the plurality of flavor pieces. This is because there generates an air flow passing through a portion which is not filled with the flavor pieces, and consequently, the air which fails to contact with the plurality of flavor pieces is increased. If the plurality of flavor pieces is a lump body (for example, an aggregate), this increases difference in airflow resistance between a lump body portion (portion filled with the flavor pieces) and the portion which is not filled with the flavor pieces. As a result, the flavor pieces located inside the lump body therefore do not come into contact with air, so that flavor is poorly added to the air through the flavor pieces located inside the lump body.

A flavor source unit according to the summary of the disclosure comprises a columnar lump body that is formed of a plurality of flavor pieces, and a cylindrical body containing the columnar lump body. The cylindrical body includes a first cylindrical body end face that forms an air inflow end, a second cylindrical body end face that forms an air outflow end, and a cylindrical body side wall connecting an outer periphery of the first cylindrical body end face and an outer periphery of the second cylindrical body end face. The columnar lump body includes a first lump body end face that forms an air inflow end, a second lump body end face that forms an air outflow end, and a lump body side face that continues into an outer periphery of the first lump body end face and an outer periphery of the second lump body end face. The columnar lump body is disposed in such a way as to block an inside space of the cylindrical body side wall by the lump body side face contacting any portion of an inner surface of the cylindrical body side wall. A first space is provided at least either between the first cylindrical body end face and the first lump body end face or between the second cylindrical body end face and the second lump body end face.

According to the summary of the disclosure, the columnar lump body is disposed in such a way as to block the inside space of the cylindrical body side wall by the lump body side face contacting any portion of the inner surface of the cylindrical body side wall. The aforementioned structure suppresses the flow of the air passing through a gap formed between the lump body side face and the inner surface of the cylindrical body side wall, and thus allows the flavor to be easily added to the air through the flavor pieces located inside the columnar lump body.

According to the summary of the disclosure, the first space is provided at least either between the first cylindrical body end face and the first lump body end face or between the second cylindrical body end face and the second lump body end face. The aforementioned structure suppresses the excessive downsizing of the flavor source unit and thus improves the ease of production and handling of the flavor source unit.

As discussed above, the flavor source unit according to the summary of the disclosure suppresses the excessive downsizing of the flavor source unit and at the same time improves the efficiency of adding the flavor to the air.

EMBODIMENT (Flavor Inhaler)

Figure 2:
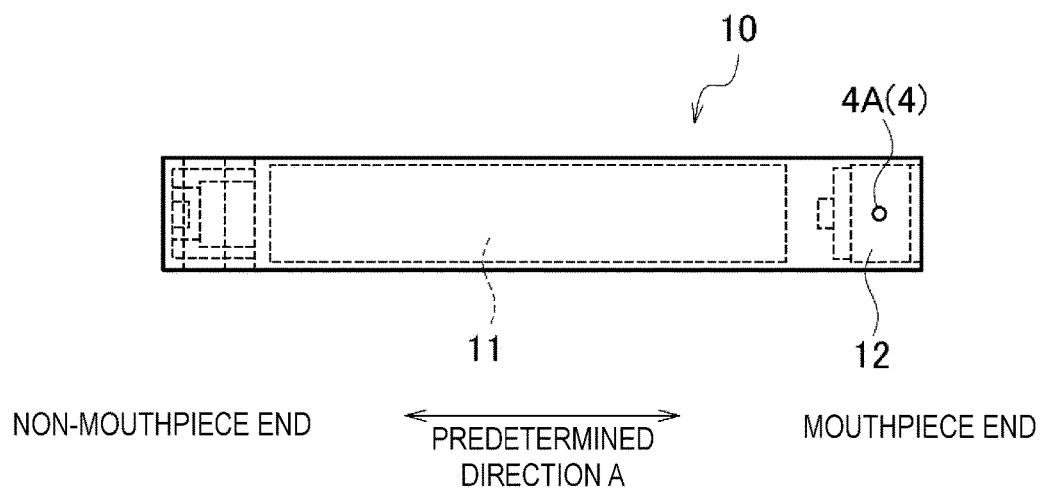
FIG. 2 is a sectional view of an electric power source unit 10 according to the embodiment.
Figure 3:
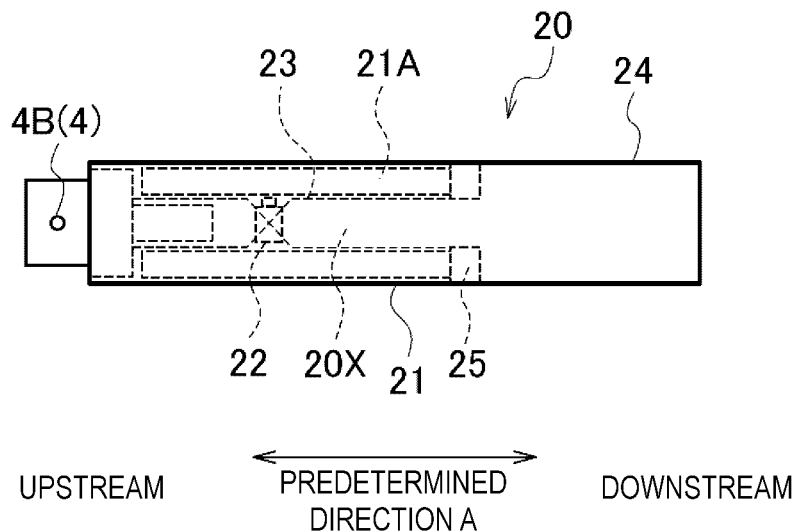
FIG. 3 is a sectional view of a first cartridge 20 according to the embodiment.
Figure 4:
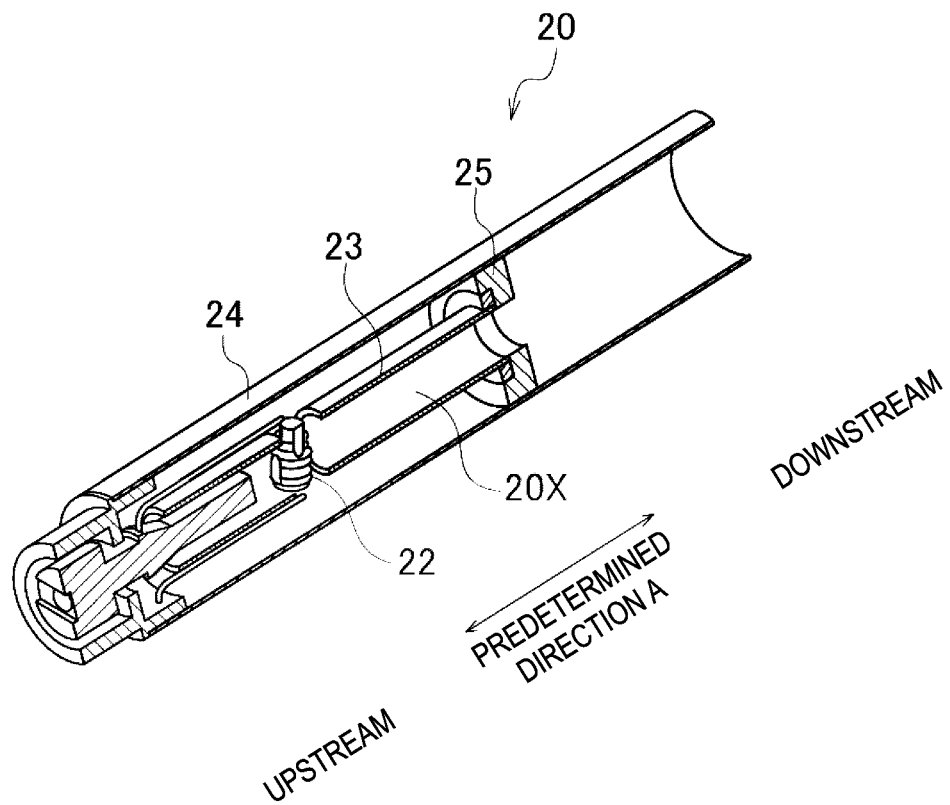
FIG. 4 shows an internal structure of the first cartridge 20 according to the embodiment.
Figure 5:
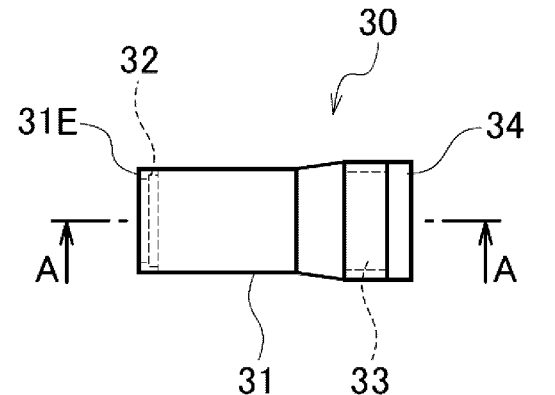
FIG. 5 is a side view of a second cartridge 30 according to the embodiment.
Figure 6:
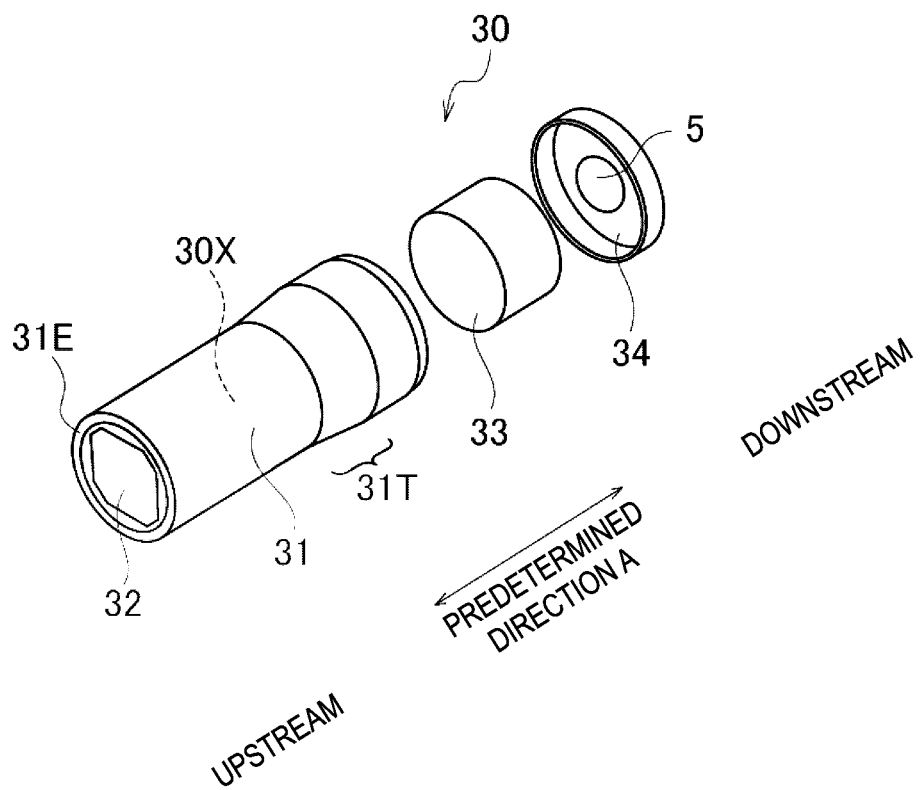
FIG. 6 is an exploded perspective view of the second cartridge 30 according to the embodiment.
Figure 7:
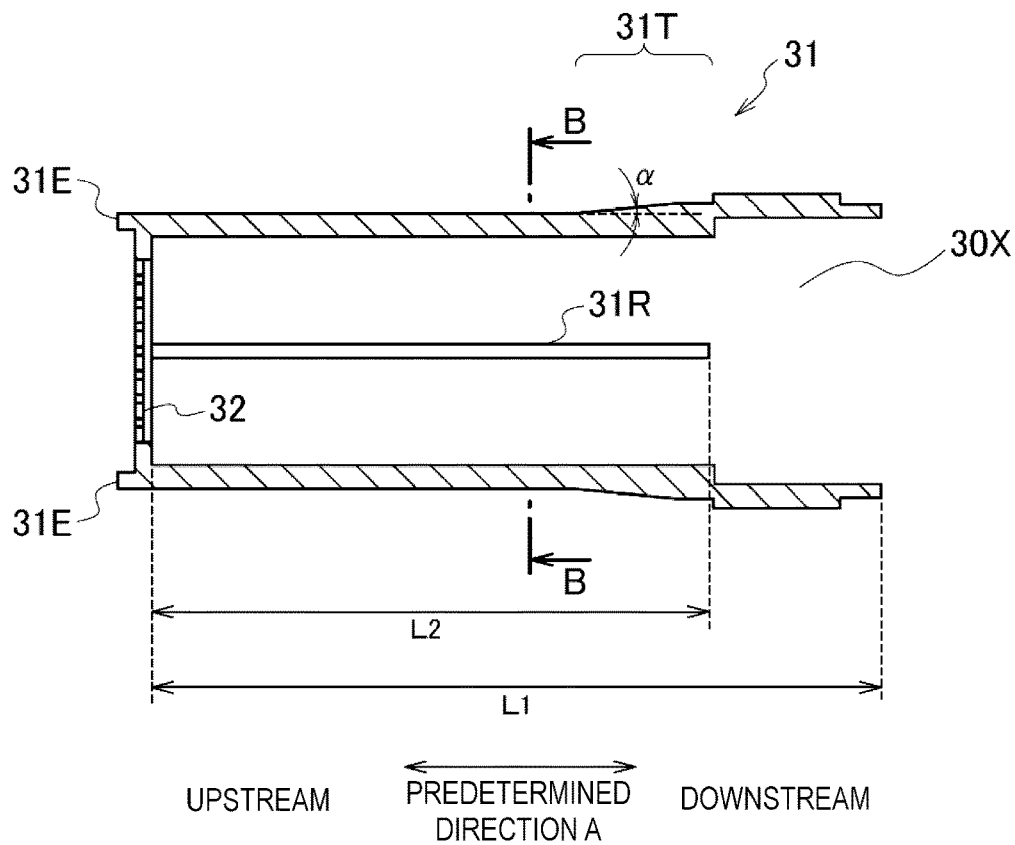
FIG. 7 is a sectional view of a cylindrical body 31 according to the embodiment (along line A-A of FIG. 5).
Figure 8:
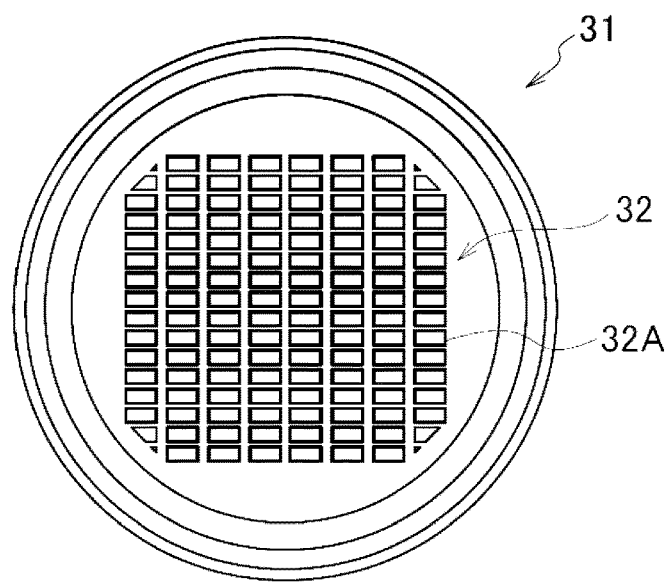
FIG. 8 is a sectional view of the cylindrical body 31 according to the embodiment (along line B-B of FIG. 7).

The following description explains a flavor inhaler according to an embodiment. FIG. 1 is a sectional view of a flavor inhaler 1 according to the embodiment. FIG. 2 is a sectional view of an electric power source unit 10 according to the embodiment. FIG. 3 is a sectional view of a first cartridge 20 according to the embodiment. FIG. 4 shows an internal structure of the first cartridge 20 according to the embodiment. It should be noted that a later-mentioned reservoir 21 is omitted in FIG. 4. FIG. 5 is a side view of a second cartridge 30 according to the embodiment. FIG. 6 is an exploded perspective view of the second cartridge 30 according to the embodiment. FIG. 7 is a sectional view of a cylindrical body 31 according to the embodiment (along line A-A of FIG. 5). FIG. 8 is a sectional view of the cylindrical body 31 according to the embodiment (along line B-B of FIG. 7). It should be noted that a columnar lump body (flavor source) is omitted in FIGS. 5 and 6.

As illustrated in FIG. 1, the flavor inhaler 1 has a shape extending in a predetermined direction A from a non-mouthpiece end toward a mouthpiece end. The flavor inhaler 1 is a tool for inhaling flavor without burning.

Specifically, the flavor inhaler 1 includes the electric power source unit 10, the first cartridge 20, and the second cartridge 30. The first cartridge 20 is attachable to/detachable from the electric power source unit 10. The second cartridge 30 is attachable to/detachable from the first cartridge 20. In short, the first cartridge 20 and the second cartridge 30 are both exchangeable. The flavor inhaler 1 includes an inlet 4 and an outlet 5, and further includes an air channel extending from the inlet 4 to the outlet 5.

As illustrated in FIG. 2, the electric power source unit 10 has a shape extending in the predetermined direction A, and at least includes a battery 11. The battery 11 may be either disposable or rechargeable. An initial value of output voltage of the battery 11 may fall in a range from 1.2 to 4.2 V, inclusive. The battery 11 has a battery capacity ranging from 100 to 1000 mAh, inclusive. The electric power source unit 10 may include an aperture 4A that forms the inlet 4 and an inhalation sensor 12 which detects a puffing action of the user. The inhalation sensor 12 is placed in an air channel.

As illustrated in FIGS. 3 and 4, the first cartridge 20 has a shape extending in the predetermined direction A. The first cartridge 20 includes the reservoir 21, an atomizing portion 22, a channel-forming body 23, an outer frame body 24, and an end cap 25. The first cartridge 20 includes a first channel 20X disposed further downstream than the atomizing portion 22. The first channel 20X functions as an aerosol channel extending in the predetermined direction A. The first cartridge 20 may include an aperture 4B that forms the inlet 4.

In the following description, as to the air channel extending from the inlet 4 to the outlet 5, a side close to the inlet 4 will be referred to as an upstream side, whereas a side close to the outlet 5 will be referred to as a downstream side.

As for the aerosol channel that forms a portion of the air channel, a side close to the atomizing portion 22 will be referred to as an upstream side, whereas a side located away from the atomizing portion 22 toward the outlet 5 will be referred to as a downstream side.

The reservoir 21 stores an aerosol source 21A. The reservoir 21 is located around the channel-forming body 23 in a cross-section orthogonal to the first channel 20X (predetermined direction A). According to the embodiment, the reservoir 21 is located in a gap between the channel-forming body 23 and the outer frame body 24. The reservoir 21 is formed of, for example, a porous body, such as resin web and cotton. The reservoir 21, however, may be formed of a tank containing the aerosol source 21A that is liquid. The aerosol source 21A contains liquid, such as glycerin and propylene glycol.

The atomizing portion 22 atomizes the aerosol source 21A not by burning, but by electric power supplied from the battery 11. According to the embodiment, the atomizing portion 22 is formed of a heating wire (coil) that is wound at a predetermined pitch. The atomizing portion 22 may be formed of a heating wire having a resistance value ranging from 1.0 to 3.0Ω, inclusive. The predetermined pitch is a value equal to or larger than such a value that does not incur contact of the heating wire, and may be a small value. The predetermined pitch may be, for example, equal to or smaller than 0.40 mm. The predetermined pitch may be constant in order to stabilize the atomization of the aerosol source 21A. The predetermined pitch is a center-to-center distance between adjacent winds of the heating wire.

The channel-forming body 23 has a shape extending in the predetermined direction A. The channel-forming body 23 has a cylindrical shape which forms the first channel 20X extending in the predetermined direction A.

The outer frame body 24 has a shape extending in the predetermined direction A. The outer frame body 24 has a cylindrical shape which contains the channel-forming body 23. According to the embodiment, the outer frame body 24 extends further downstream than the end cap 25 and detachably holds the second cartridge 30.

The end cap 25 is a cap which blocks the gap between the channel-forming body 23 and the outer frame body 24 from the downstream side. The end cap 25 suppresses a leakage of the aerosol source 21A stored in the reservoir 21 into the channel 20X and the second cartridge 30 side.

According to the embodiment, the first cartridge 20 is an example of the atomizing unit which is placed further upstream than the second cartridge 30.

The second cartridge 30 is installed in a body of the flavor inhaler 1. According to the embodiment, the second cartridge 30 is connected to the first cartridge 20. The second cartridge 30 particularly includes a portion which is inserted in the outer frame body 24 of the first cartridge 20.

According to the embodiment, the second cartridge 30 is an example of the flavor source unit including the columnar lump body formed of the plurality of flavor pieces and the cylindrical body 31 containing the columnar lump body.

As illustrated in FIGS. 5 and 6, the second cartridge 30 has a shape extending in the predetermined direction A. The second cartridge 30 includes the cylindrical body 31, a mesh body 32, a filter 33, and a cap 34. The cylindrical body 31 includes, as an aerosol channel, a second channel 30X disposed further downstream than the first channel 20X.

According to the second cartridge 30, the aerosol atomized by the atomizing portion 22 passes through an inside space of the cylindrical body 31, and the flavor is thus added to the aerosol through the columnar lump body. It should be noted that the embodiment makes it possible to add the flavor to the aerosol without heating the plurality of flavor pieces that forms the columnar lump body. It also should be noted that the aerosol is not substantially generated from the flavor source 31A.

A maximum size of the second cartridge 30 in the predetermined direction A may be 40 mm or less. Furthermore, the maximum size of the second cartridge 30 in the predetermined direction A may be 25 mm or less. On the other hand, a minimum size of the second cartridge 30 in the predetermined direction A may be 5 mm or more. Furthermore, the minimum size of the second cartridge 30 in the predetermined direction A may be 1 mm or more. A maximum size of the second cartridge 30 in a direction orthogonal to the predetermined direction A may be 20 mm or less. Furthermore, the maximum size of the second cartridge 30 in the direction orthogonal to the predetermined direction A may be 10 mm or less. On the other hand, a minimum size of the second cartridge 30 in the direction orthogonal to the predetermined direction A may be 3 mm or more. Furthermore, the minimum size of the second cartridge 30 in the direction orthogonal to the predetermined direction A may be 1 mm or more.

The cylindrical body 31 has a cylindrical shape. The cylindrical body 31 forms the second channel 30X that continues from an air inflow end (first cylindrical body end face 311 described later) into an air outflow end (second cylindrical body end face 312 described later). The columnar lump body which adds the flavor to the aerosol is contained in the inside space (second channel 30X) of the cylindrical body 31. The first channel 20X may be small in size in order to ensure the volume of the reservoir 21 which stores the columnar lump body in a cross-section orthogonal to the aerosol channel (predetermined direction A). Accordingly, if the second cartridge 30 is contained in the outer frame body 24 having constant sectional area across the aerosol channel (predetermined direction A), it is consequently likely that the second channel 30 is larger in size than the first channel 20X.

According to the embodiment, as illustrated in FIGS. 6 and 7, the cylindrical body 31 may include a protruding portion 31E which protrudes from an outer edge of an end wall (mesh body 32 in this case) which is located upstream of the cylindrical body 31 in the cross-section orthogonal to the aerosol channel (predetermined direction A) to the upstream side (a side close to the channel-forming body 23 or the end cap 25 in the embodiment). The protruding portion 31E may be formed continuously along the outer edge of the mesh body 32 located upstream of the cylindrical body 31 or may be formed discontinuously along the outer edge of the cylindrical body 31. If there is a gap between the outer frame body 24 and the cylindrical body 31, the protruding portion 31E may be formed continuously along the outer edge of the mesh body 32 located upstream of the cylindrical body 31. This suppresses accumulation of the aerosol in a space provided in an upstream portion of a tapered portion 31T.

According to the embodiment, as illustrated in FIGS. 6 and 7, the cylindrical body 31 may include, in an outer surface thereof, the tapered portion 31T expanding from the upstream side toward the downstream side. The tapered portion 31T may be included in a portion of the outer surface of the cylindrical body 31. The tapered portion 31T has a taper angle α ranging, for example, approximately 3 to 5 degrees, inclusive.

According to the embodiment, as illustrated in FIG. 7, a rib 31R may be disposed in an inner surface of the cylindrical body 31. The rib 31R extends from the upstream side toward the downstream side in the predetermined direction A. The rib 31R is not particularly limited in number and may comprise two or more ribs 31R. A downstream end portion of the rib 31R does not have to reach a downstream end face of the cylindrical body 31. For example, length L2 between the mesh body 32 and the downstream end portion of the rib 31R is shorter than length L1 between the mesh body 32 and the downstream end face of the cylindrical body 31 in the predetermined direction A. In other words, the downstream end portion of the rib 31R may be in contact with the filter 33 with the filter 33 inserted in the cylindrical body 31, instead of reaching the downstream end portion of the cylindrical body 31.

The mesh body 32 is disposed further upstream (non-mouthpiece side) than the flavor source 31A. According to the embodiment, the mesh body 32 is disposed in an upstream end portion of the cylindrical body 31. If the mesh body 32 disposed in the cylindrical body 31 is very small, the cylindrical body 31 and the mesh body 32 may be formed by integral molding in order to ensure the strength of the mesh body 32. In short, according to the embodiment, the mesh body 32 is a part of the cylindrical body 31. In such a case, the cylindrical body 31 and the mesh body 32 may be made of resin. The resin which can be used is, for example, one or more resins selected from among polypropylene, polyethylene terephthalate, polyethylene resin, and acrylonitrile-butadiene-styrene resin. In view of moldability and texture, the resin may be polypropylene. The cylindrical body 31 and the mesh body 32 are formed by metallic molding or injection molding.

The filter 33 is made of predetermined fiber and has such roughness that raw material particles do not pass through the filter 33. The filter 33 is placed further downstream than a columnar lump body 320. The filter 33 is, for example, an acetate filter. The cap 34 is disposed further downstream (mouthpiece side) than the filter 33. The cap 34 includes an outlet 5 and may form a mouthpiece to be held in the user's mouth. The cylindrical body 31 (including the mesh body 32 in this case), the filter 33, and the cap 34 may be bonded or welded to one another.

Figure 9:
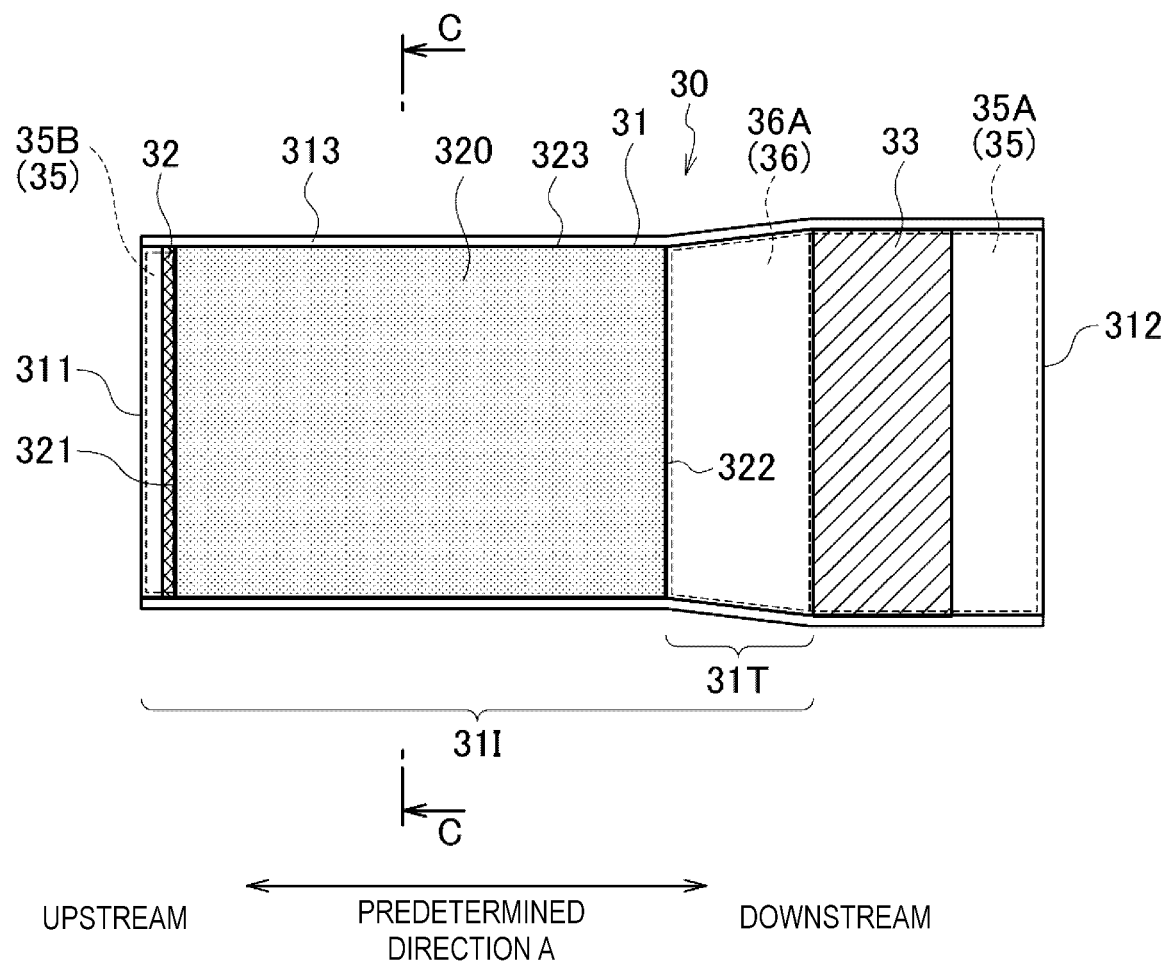
FIG. 9 is a sectional view of a second cartridge 30 according to the embodiment.

According to the embodiment, as illustrated in FIG. 9, the second cartridge 30 comprises the columnar lump body 320 that is formed of a plurality of flavor pieces, and the cylindrical body 31 containing the columnar lump body 320. The cylindrical body 31 includes a first cylindrical body end face 311 that forms an air inflow end, a second cylindrical body end face 312 that forms an air outflow end, and a cylindrical body side wall 313 connecting an outer periphery of the first cylindrical body end face 311 and an outer periphery of the second cylindrical body end face 312. The columnar lump body 320 includes a first lump body end face 321 that forms the air inflow end, a second lump body end face 322 that forms an air outflow end, and a lump body side face 323 that continues into an outer periphery of the first lump body end face and an outer periphery of the second lump body end face 322.

Figure 10:
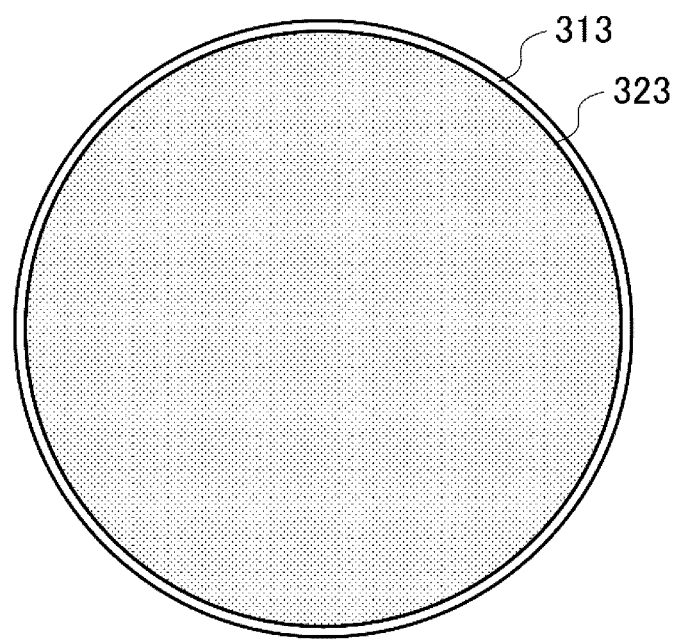
FIG. 10 is a sectional view of the second cartridge 30 according to the embodiment.

The columnar lump body 320 is disposed in such a way as to block an inside space (namely, the second channel 30X) of the cylindrical body side wall 313 by the lump body side face 323 contacting any portion of the inner surface of the cylindrical body side wall 313. The term "block" here means that the columnar lump body 320 exists in the inside space of the cylindrical body side wall 313 so that there is no air channel that does not extend from the air inflow end toward the air outflow end through the inside of the columnar lump body 320, for example, so that there is no air channel with a low airflow resistance, which is formed between the inner surface of the cylindrical body side wall 313 and the lump body side face 323, except the air channel extending through the columnar lump body 320. As illustrated in FIG. 10, the entire lump body side face 323 is in contact with the inner surface of the cylindrical body side wall 313 in a C-C section of FIG. 9.

The lump body side face 323 may be fixed to the inner surface of the cylindrical body side wall 313. The term "fix" may mean that the columnar lump body 320 is positioned in the inner surface of the cylindrical body side wall 313 without being displaced during normal use, for example, that the columnar lump body 320 is not displaced in the inside space of the cylindrical body side wall 313 due to static friction between the lump body side face 323 and the inner surface of the cylindrical body side wall 313. The aforementioned state is achieved by the lump body side face 323 being bonded to the inner surface of the cylindrical body side wall 313 by viscosity of the columnar lump body 320. Alternatively, the lump body side face 323 may be bonded with an adhesive agent to the inner surface of the cylindrical body side wall 313.

A first space 35 is provided at least either between the first cylindrical body end face 311 and the first lump body end face 321 or between the second cylindrical body end face 312 and the second lump body end face 322. According to an example illustrated in FIG. 9, a first space 35A is provided between the second cylindrical body end face 312 and the second lump body end face 322. Since there is provided the protruding portion 31E protruding from the outer edge of the mesh body 32 to the upstream side, a first space 35B is provided between the first cylindrical body end face 311 and the first lump body end face 321.

The cylindrical body 31 includes the mesh body 32 (first end wall) which demarcates the inside space of the cylindrical body side wall 313 on a side close to the first cylindrical body end face 311, and the filter 33 (second end wall) which demarcates the inside space of the cylindrical body side wall 313 on a side close to the second cylindrical body end face 312. A second space 36 that forms a portion of the first space 35 is provided at least either between the mesh body 32 and the first lump body end face 321 or between the filter 33 and the second lump body end face 322. According to the example illustrated in FIG. 9, a second space 36A is provided between the filter 33 and the second lump body end face 322. In other words, the filter 33 is exposed to the second space 36A and away from the second lump body end face 322 to avoid contact with the second lump body end face 322. In other words, a wall body facing the second space 36 is the filter 33 (second end wall). According to the example illustrated in FIG. 9, the second space 36 is not provided between the mesh body 32 and the first lump body end face 321, and the mesh body 32 is in contact with the first lump body end face 321.

As described above, the second cartridge 30 is detachably held by a body (first cartridge 20) of a flavor inhaler 100. More specifically, the cylindrical body 31 includes an inserted portion 311 which is inserted into the outer frame body 24 of the first cartridge 20. The inserted portion 311 includes a tapered portion 31T as a connect portion which is mechanically connected to the body of the flavor inhaler 100. The second space 36A that forms a portion of the first space 35A is adjacent to the connect portion (tapered portion 31T). The term "adjacent" here means that at least a portion of a space surrounded by the connect portion (tapered portion 31T) overlaps the second space 36A.

The second space 36 may have a volume of 5 to 90 percent of a capacity of a space surrounded by the mesh body 32 (first end wall), the filter 33 (second end wall), and the cylindrical body side wall 313 (hereinafter, referred to as reference capacity). A lower limit of the volume of the second space 36 relative to the reference capacity is preferably 10 percent, and more preferably 20 percent. Furthermore, the lower limit of the volume of the second space 36 relative to the reference capacity is preferably 30 percent, and more preferably 40 percent. An upper limit of the volume of the second space 36 relative to the reference capacity is preferably 70 percent, and more preferably 50 percent. The lower limit of the volume of the second space 36 relative to the reference capacity may be any value selected from among 5, 10, 20, 30 and 40 percent, and the upper limit of the volume of the second space 36 relative to the reference capacity may be any value selected from among 90, 70 and 50 percent.

The first cylindrical body end face 311 may be the same shape and size as the second cylindrical body end face 312. The cross-section of the cylindrical body 31, which is orthogonal to the predetermined direction A, may keep the same shape and size across the entire cylindrical body 31 in the predetermined direction A. The term "same" here means that the shape and the size are not significantly changed. The term is used, taking into account a change in shape and size due to the tapered portion 31T.

The first lump body end face 321 may be the same shape and size as the second lump body end face 322. A cross-section of the columnar lump body 320, which is orthogonal to the predetermined direction A, may keep the same shape and size across the entire columnar lump body 320 in the predetermined direction A. The term "same" here is the same concept as the foregoing.

The columnar lump body 320 is formed of the plurality of flavor pieces as described above. The plurality of flavor pieces comprise flavor pieces which add flavor to the aerosol generated by the flavor inhaler 1. The flavor pieces which may be used include cut tobacco obtained by shredding tobacco material, and granulated tobacco obtained by pulverizing tobacco material. The flavor pieces which may be used include raw material particles obtained by shredding or pulverizing other plants than tobacco (for example, mints, herbs, etc.). The plurality of flavor pieces may include at least one of an aroma chemical and a binder. Menthol or the like may be used as the flavor. As the binder, HPC (hydroxypropylcellulose), pullulan, CMC (carboxymethylcellulose), CMC-Na or the like may be used. The amount of the flavor and of the binder may be determined as appropriate. For example, the amount of the flavor may be 5 to 20 percent by weight, and the amount of the binder may be 3 percent to 7 percent by weight.

A compression degree of the plurality of flavor pieces may fall in a range from 22 to 34 percent, inclusive. Preferably, the compression degree of the plurality of flavor pieces may fall in a range from 29 to 34 percent, inclusive. The columnar lump body 320 formed at the compression degree which falls in the aforementioned value range suppresses deformation of the column-like shape of the columnar lump body 320. The plurality of flavor pieces may have a loose bulk density ranging from 0.40 to 0.54 g/cm$^3$, inclusive. The plurality of flavor pieces may have a tight bulk density ranging from 0.68 to 0.71 g/cm$^3$, inclusive. A bulk density of the columnar lump body 320 may fall in a range from 130 to 160 percent, inclusive, of the loose bulk density of the plurality of flavor pieces. The bulk density of the columnar lump body 320 may be higher than the tight bulk density of the plurality of flavor pieces. Each of the plurality of flavor pieces may have a size ranging from 0.2 to 1.4 mm, inclusive (shredding width or particle diameter).

A loose bulk density (A) is obtained by the steps of placing a container with a low wall effect under a coarse sieve (standard: 1.7 mm), feeding the flavor pieces into the container through the sieve, and dividing the weight of the flavor pieces fed into the container by the volume of the container. To obtain a tight bulk density (P), a cap is secured to the container, and the container is filled with the flavor pieces while being tapped. The container is tapped 180 times at a tapping stroke of 18 mm. After the tapping is finished, the weight of the flavor pieces contained in the container is divided by the volume of the container, thus obtaining the tight bulk density (P). A compression degree (C) is a value calculated by a formula: $C=(P-A)/P\times100(\%)$. The aforementioned values can be measured, for example, using a powder tester made by Hosokawa Micron Corporation.

Since the columnar lump body 320 is formed by compressing the plurality of flavor pieces, it is possible to maintain the shape of the columnar lump body 320 and prevent uneven distribution of the flavor pieces within the columnar lump body 320. Furthermore, the columnar lump body 320 is formed by compressing the plurality of flavor pieces or a primary compressed body formed of the plurality of flavor pieces within the cylindrical body 31, which makes it possible to prevent a gap from being provided between the inner surface of the cylindrical body side wall 313 and the lump body side face 323.

Operation and Advantageous Effects

According to the embodiment, the columnar lump body 320 is disposed in such a way as to block the inside space of the cylindrical body side wall 313 by the lump body side face 323 contacting any portion of the inner surface of the cylindrical body side wall 313. The foregoing constitution suppresses the flow of the air passing through a gap formed between the lump body side face 323 and the inner surface of the cylindrical body side wall 313, and thus makes it easy to add the flavor to the air through the flavor pieces located inside the columnar lump body 320.

According to the embodiment, the first space 35 including the second space 36A is provided at least between the second cylindrical body end face 312 and the second lump body end face 322. The first space 35 may be provided between the first cylindrical body end face 311 and the first lump body end face 321. The foregoing constitution suppresses the excessive downsizing of the second cartridge 30 and thus improves the ease of production and handling of the second cartridge 30.

As described above, the second cartridge 30 according to the embodiment makes it possible to suppress the excessive downsizing of the second cartridge 30 and also improve the efficiency of the flavor addition to air.

According to the embodiment, the columnar lump body 320 is formed of the plurality of flavor pieces. This constitution keeps the columnar lump body 320 blocking the inside space of the cylindrical body side wall 313, and therefore suppresses a deterioration in efficiency of the flavor addition to air.

According to the embodiment, the lump body side face 323 may be fixed to the inner surface of the cylindrical body side wall 313. This constitution suppresses movement of the columnar lump body 320 within the inside space of the cylindrical body side wall 313 and suppresses collapse of the columnar lump body 320. It is therefore easy to maintain the state in which the inside space of the cylindrical body side wall 313 is blocked by the columnar lump body 320.

According to the embodiment, the second space 36 is provided between the filter 33 and the second lump body end face 322. This constitution further suppresses the excessive downsizing of the second cartridge 30. Moreover, the filter 33 does not contact the columnar lump body 320, which suppresses the staining and clogging of the filter 33, and also suppresses the transfer of ingredients from the columnar lump body 320 to the filter. It is also possible to downsize the filter 33 in the predetermined direction A without changing the size of the second cartridge 30 as a whole.

According to the embodiment, the mesh body 32 (first end wall) is in contact with the first lump body end face 321. It is possible, with the foregoing constitution, to efficiently block the gap between the lump body side face 323 and the inner surface of the cylindrical body side wall 313 by compressing the plurality of flavor pieces or the primary compressed body of the plurality of flavor pieces, which is located in the cylindrical body 31, while pressing the plurality of flavor pieces or the primary compressed body against the mesh body 32.

According to the embodiment, the second space 36A that forms a portion of the first space 35A is adjacent to the connect portion (tapered portion 31T). This makes it possible to suppress the collapse of the columnar lump body 320, which is caused by the pressure applied to the connect portion when the second cartridge is installed in the body of the flavor inhaler 100. It is therefore easy to maintain the state in which the inside space of the cylindrical body side wall 313 is blocked by the columnar lump body 320.

Modified Example 1

A modified example 1 of the embodiment will be now described. The following description relates mainly to differences from the embodiment.

Specifically, according to the embodiment, the second space 36A is provided between the filter 33 (second end wall) and the second lump body end face 322, and the mesh body 32 (first end wall) is in contact with the first lump body end face 321.

Figure 11:
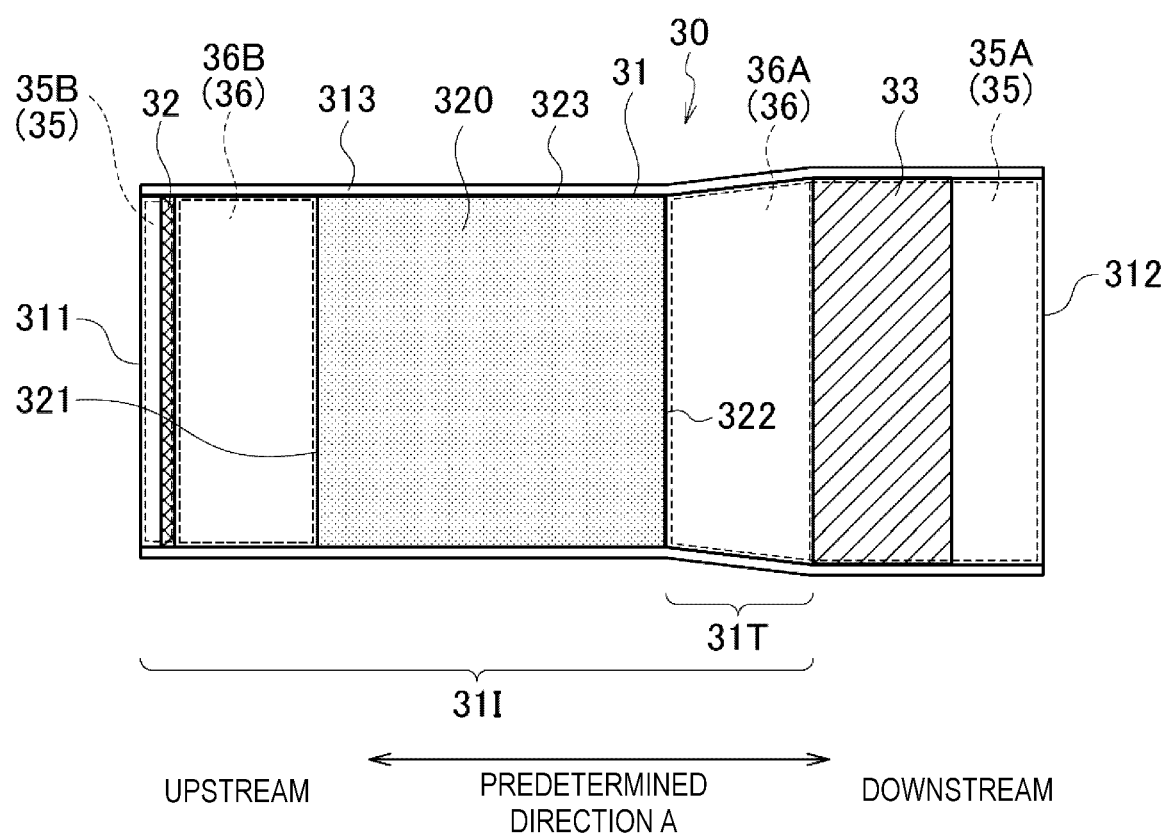
FIG. 11 is a sectional view of a second cartridge 30 according to a modified example 1.

According to the modified example 1, as illustrated in FIG. 11, the second space 36A is provided between the filter 33 and the second lump body end face 322, and a second space 36B is provided between the mesh body 32 and the first lump body end face 321. The second space 36B forms a portion of the first space 35B provided between the first cylindrical body end face 311 and the first lump body end face 321.

Modified Example 2

A modified example 2 of the embodiment will be now described. The following description relates mainly to differences from the embodiment.

Specifically, according to the embodiment, the second space 36A is provided between the filter 33 (second end wall) and the second lump body end face 322, and the mesh body 32 (first end wall) is in contact with the first lump body end face 321.

Figure 12:
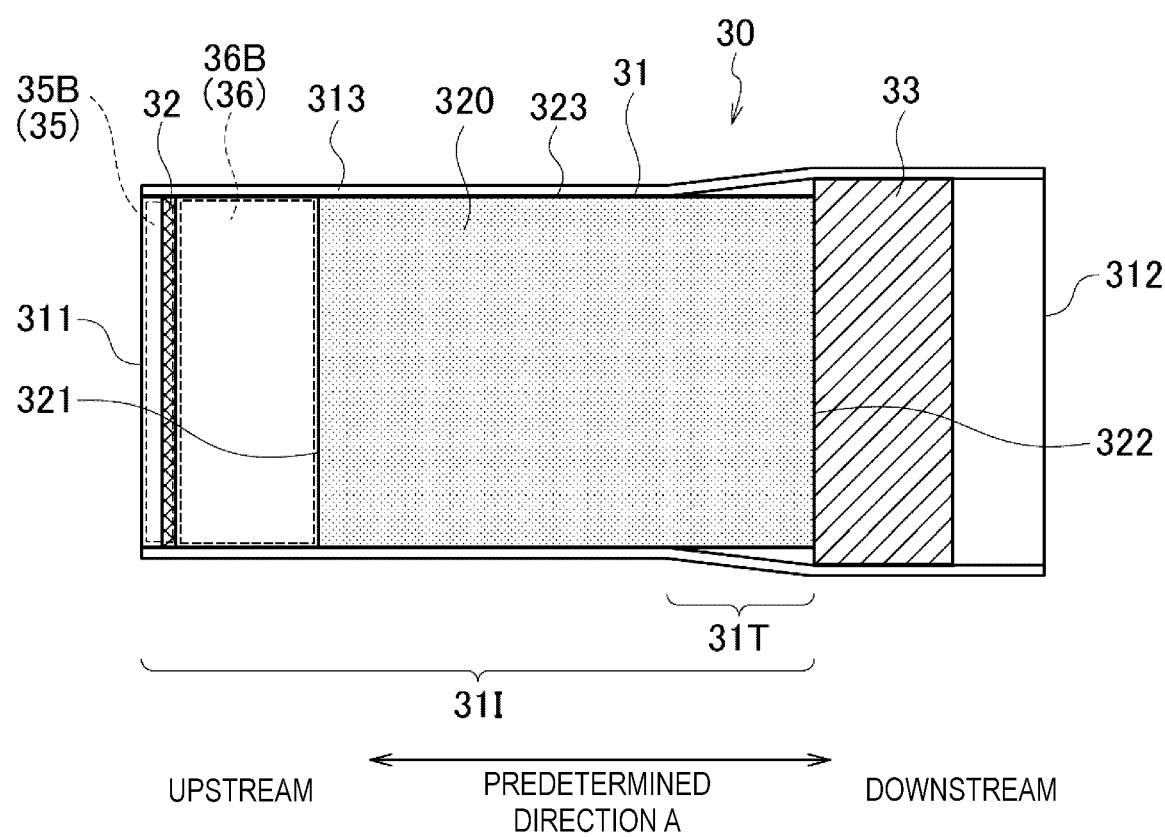
FIG. 12 is a sectional view of a second cartridge 30 according to a modified example 2.

According to the modified example 2, as illustrated in FIG. 12, the second space 36 is not provided between the filter 33 and the second lump body end face 322, so that the filter 33 is in contact with the second lump body end face 322. On the other hand, the second space 36B is provided between the mesh body 32 and the first lump body end face 321. The second space 36B forms a portion of the first space 35B provided between the first cylindrical body end face 311 and the first lump body end face 321.

FIG. 12 describes the invention using the same constitution as in FIG. 9 for the sake of ease of comparison. The modified example 2, however, is not limited to the aforementioned constitution. The first end wall may be the filter 33, instead of the mesh body 32. The second end wall may be the mesh body 32, instead of the filter 33.

Modified Example 3

A modified example 3 of the embodiment will be now described. The following description relates mainly to differences from the embodiment.

Specifically, according to the embodiment, the cross-section orthogonal to the second channel 30X (predetermined direction A) includes a cross-section in which the entire lump body side face 323 is in contact with the inner surface of the cylindrical body side wall 313.

Figure 13:
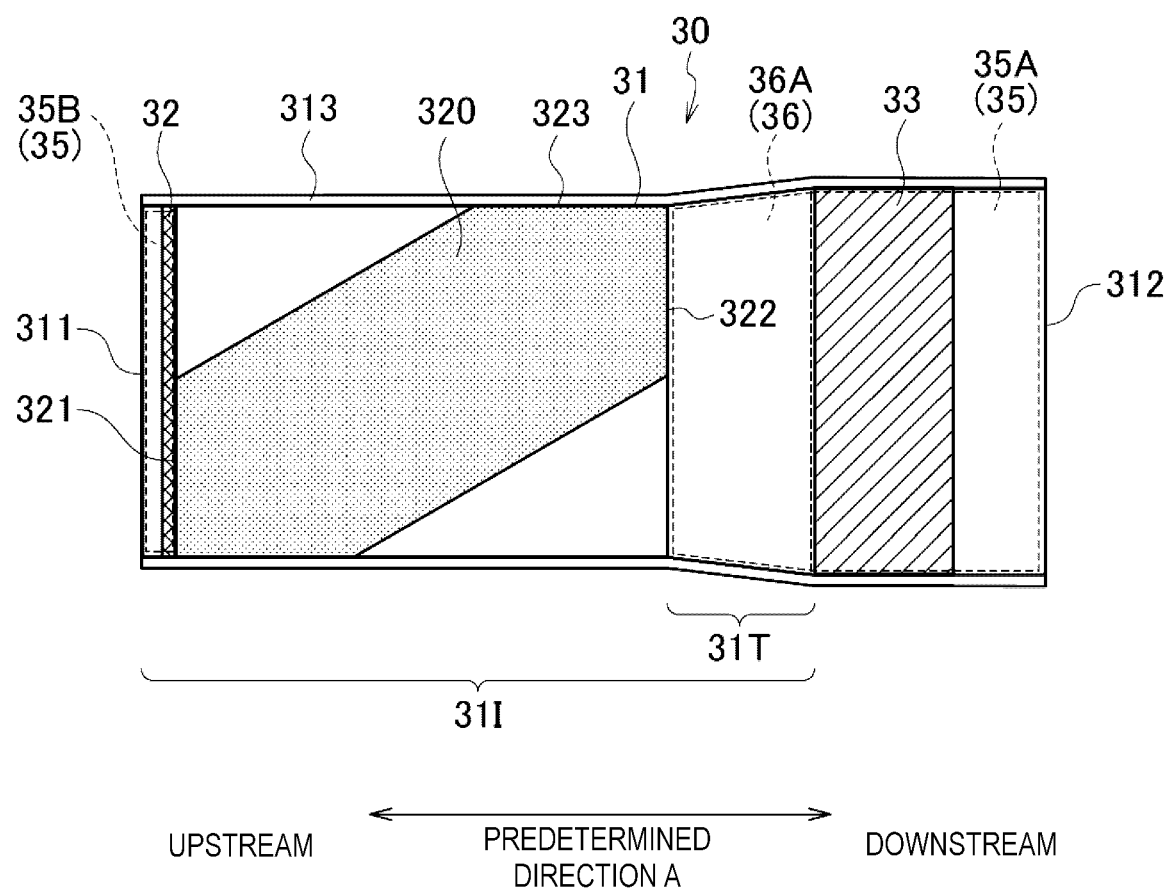
FIG. 13 is a sectional view of a second cartridge 30 according to a modified example 3.

According to the modified example 3, as illustrated in FIG. 13, the cross-section orthogonal to the second channel 30X (predetermined direction A) does not include the cross-section in which the entire lump body side face 323 is in contact with the inner surface of the cylindrical body side wall 313. However, in the modified example 3, the columnar lump body 320 is disposed in such a way as to block the inside space (namely, the second channel 30X) of the cylindrical body side wall 313 by the lump body side face 323 contacting any portion of the inner surface of the cylindrical body side wall 313, as in the embodiment. In other words, there is no air channel which does not pass through the columnar lump body 320 from the upstream side toward the downstream side.

Modified Example 4

A modified example 4 of the embodiment will be now described. The following description relates mainly to differences from the embodiment.

Specifically, according to the embodiment, the second space 36 that forms a portion of the first space 35 is provided at least either between the mesh body 32 (first end wall) and the first lump body end face 321 or between the filter 33 (second end wall) and the second lump body end face 322.

Figure 14:
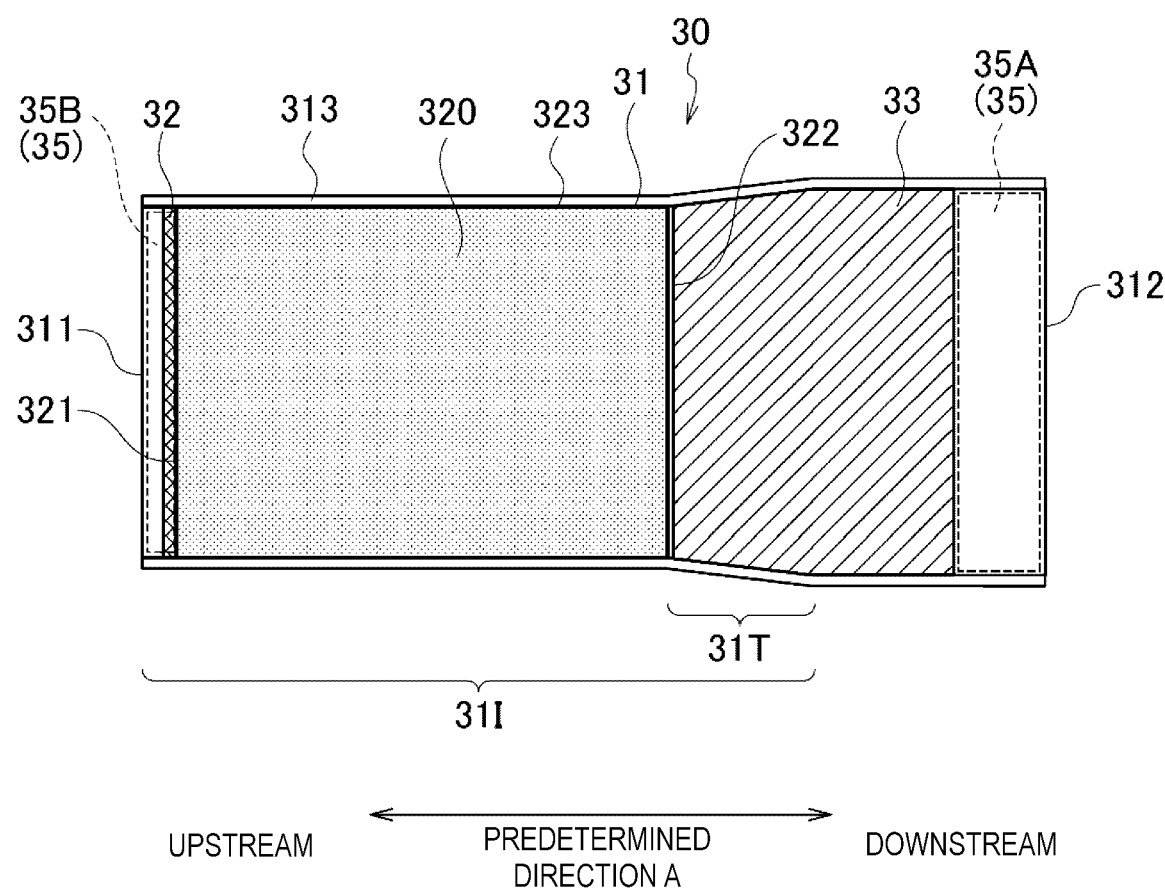
FIG. 14 is a sectional view of a second cartridge 30 according to a modified example 4.

According to the modified example 4, however, at least either mesh body 32 or the filter 33 fills in the first space 35 in such a manner as to contact the columnar lump body 320. According to an example illustrated in FIG. 14, the filter 33 fills in the first space 35 in such a manner as to contact the columnar lump body 320. In other words, the second space 36 is not provided between the filter 33 and the second lump body end face 322.

Modified Example 5

A modified example 5 of the embodiment will be now described. The following description relates mainly to differences from the embodiment.

Figure 15:
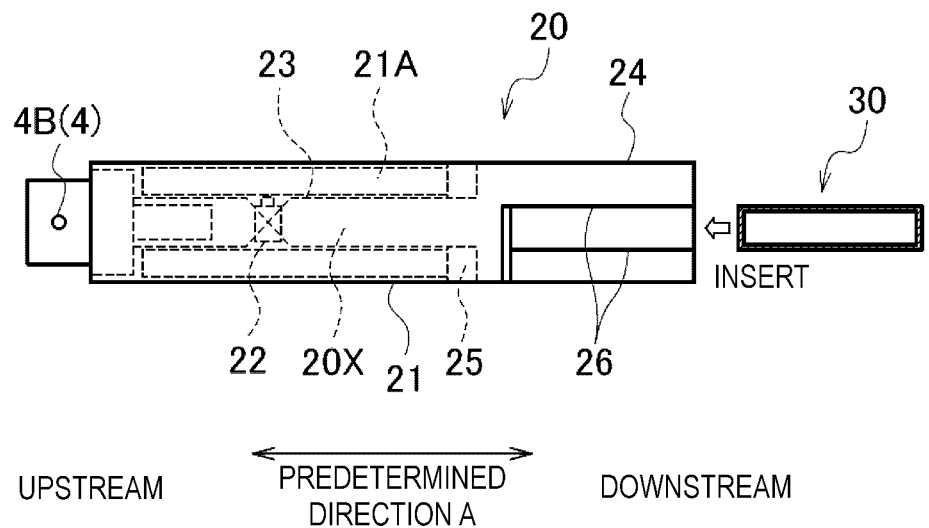
FIG. 15 is a view for describing a method of installing a second cartridge 30 according to a modified example 5.
Figure 16:
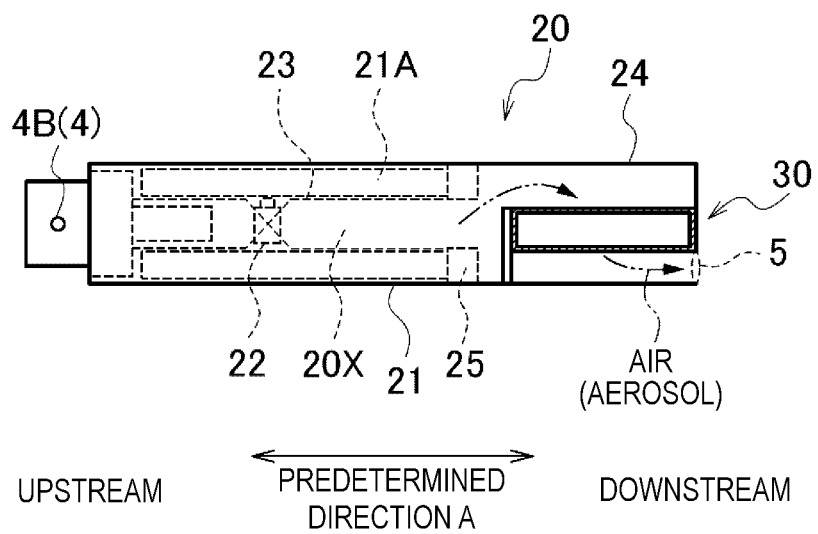
FIG. 16 is a view for describing a method of installing the second cartridge 30 according to the modified example 5.

As illustrated in FIGS. 15 and 16, the second cartridge 30 is installed in the body (first cartridge 20) of the flavor inhaler 100 so as to demarcate the aerosol channel. To be specific, as illustrated in FIG. 15, the second cartridge 30 is inserted in the first cartridge 20 along a guide rib 26 which is disposed in the first cartridge 20. The aerosol channel is thus demarcated by the second cartridge 30 as illustrated in FIG. 16. According to an example illustrated in FIG. 16, an upper surface of the second cartridge 30 is an air inflow end, and a lower surface of the second cartridge 30 is an air outflow end.

Figure 17:
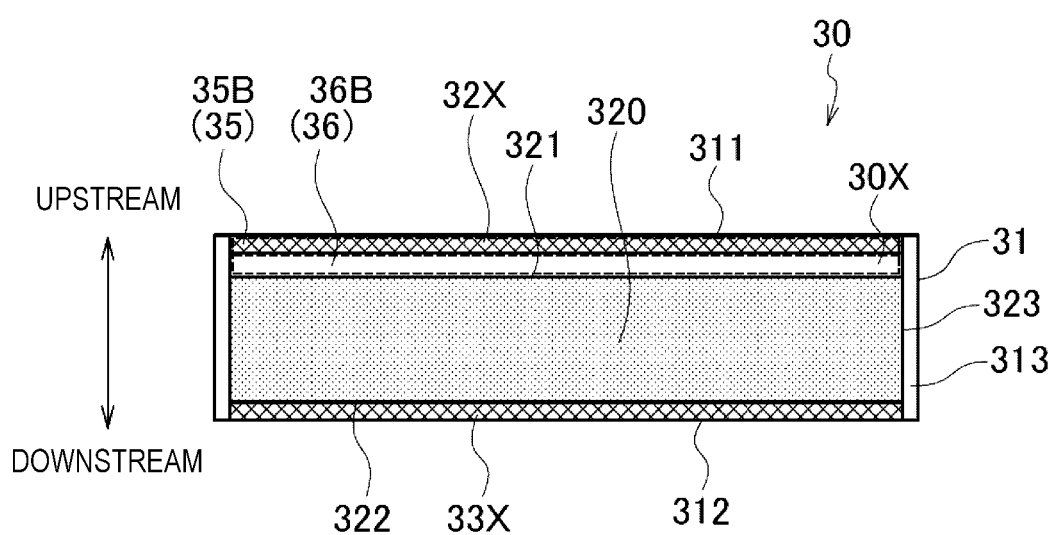
FIG. 17 is a sectional view of the second cartridge 30 according to the modified example 5.

As illustrated in FIG. 17, the cylindrical body 31 includes a first end wall 32X which demarcates the inside space of the cylindrical body side wall 313 on a side close to the first cylindrical body end face 311 which forms the air inflow end, and a second end wall 33X which demarcates the inside space of the cylindrical body side wall 313 on a side close to the second cylindrical body end face 312 which forms the air outflow end. The first end wall 32X and the second end wall 33X are mesh bodies or filters.

The first space 35B is provided between the first cylindrical body end face 311 and the first lump body end face 321. The second space 36B that forms a portion of the first space 35B is provided between the first end wall 32X and the first lump body end face 321. According to the modified example 5, the columnar lump body 320 is disposed in such a way as to block the inside space (namely, the second channel 30X) of the cylindrical body side wall 313 by the lump body side face 323 contacting any portion of the inner surface of the cylindrical body side wall 313.

As described above, a direction in which air flows through the second cartridge 30 as a single body (orientation of the second channel 30X that continues from the first cylindrical body end face 311 to the second cylindrical body end face 312) may differ from the orientation of the predetermined direction A. Even in such a case, it is possible to suppress the flow of the air passing through the gap between the lump body side face 323 and the inner surface of the cylindrical body side wall 313, making it easy to add the flavor to the air through the flavor pieces located inside the columnar lump body 320, as in the embodiment.

Other Embodiments

The invention has been described with reference to the embodiment. It should be noted that the discussion and drawings which form a part of the disclosure are not intended to limit the invention. Various alternate embodiments, examples, and operation technology should be evident to those in the art from the foregoing disclosure.

According to the embodiment, the cylindrical body 31 includes the mesh body 32 functioning as the first end wall disposed on the upstream side. However, the embodiment is not limited to such constitution. The first end wall may be the filter 33. In other words, the wall body facing the second space may be the first end wall. The cylindrical body 31 includes the filter 33 functioning as the second end wall disposed on the downstream side. However, the embodiment is not limited to such constitution. The second end wall may be the mesh body 32.

The embodiment has been described on the premise that the second end wall is the filter 33. However, the embodiment is not limited to such constitution. The second end wall may include other members in addition to the filter 33. For example, the second end wall may be the filter 33 and the cap 34.

According to the embodiment, the cylindrical body 31 includes the tapered portion 31T as the connect portion which is mechanically connected to the body of the flavor inhaler 100. However, the embodiment is not limited to such constitution. The connect portion only has to be a portion which is mechanically connected to the body of the flavor inhaler 100. The connect portion is a portion which is applied with pressure when the second cartridge is installed in the body of the flavor inhaler 100. The connect portion may be a stepped portion for locking the second cartridge to the body of the flavor inhaler 100 or may be an external thread for threadably installing the second cartridge in the body of the flavor inhaler 100.

According to the embodiment, since the protruding portion 31E is provided, which protrudes from the outer edge of the mesh body 32 toward the upstream side, the first space 35B is provided between the first cylindrical body end face 311 and the first lump body end face 321. However, the embodiment is not limited to such constitution. The embodiment may be so configured that the mesh body 32 (first end wall) includes the first cylindrical body end face 311, and therefore, the first space 35B does not substantially exist between the first cylindrical body end face 311 and the first lump body end face 321.

FIGS. 9 and 11 to 14 illustrate the cases in which the cylindrical body 31 does not include the cap 34, so that the cap 34 is omitted from these drawings. However, the embodiment and the modified examples are not limited to such constitution. For example, the cylindrical body 31 may be considered as a member which includes the cap 34. In such a case, the second cylindrical body end face 312 is formed of an upstream end face of the cap 34. As already explained in the embodiment, the second cylindrical body end face 312 may be the same shape and size as the first cylindrical body end face 311.

The entire disclosure of Japanese Patent Application No. 2017-104173 (filed on May 26, 2017) is incorporated herein by reference in its entirety.

INDUSTRIAL APPLICABILITY

One aspect provides a flavor source unit and the flavor inhaler, which make it possible to improve the efficiency of adding the flavor to the air while suppressing the excessive downsizing of the flavor source unit.

The invention claimed is:

1. A flavor source unit for a non-burning flavor inhaler comprising:
   a columnar lump body that is formed of a plurality of flavor pieces, and
   a cylindrical body containing the columnar lump body,
   the cylindrical body including a first cylindrical body end face that forms an air inflow end, a second cylindrical body end face that forms an air outflow end, and a cylindrical body side wall connecting an outer periphery of the first cylindrical body end face and an outer periphery of the second cylindrical body end face,
   the columnar lump body including a first lump body end face that forms an air inflow end, a second lump body end face that forms an air outflow end, and a lump body side face that continues into an outer periphery of the first lump body end face and an outer periphery of the second lump body end face,
   the columnar lump body being disposed in such a way as to block an inside space of the cylindrical body side wall by the lump body side face contacting any portion of an inner surface of the cylindrical body side wall,
   wherein a first space is provided at least either between the first cylindrical body end face and the first lump body end face or between the second cylindrical body end face and the second lump body end face.

2. The flavor source unit as described in claim 1, comprising:
   a first end wall which demarcates the inside space of the cylindrical body side wall on a side close to the first cylindrical body end face, and
   a second end wall which demarcates the inside space of the cylindrical body side wall on a side close to the second cylindrical body end face,
   wherein a second space that forms a portion of the first space is provided at least either between the first end wall and the first lump body end face or between the second end wall and the second lump body end face.

3. The flavor source unit as described in claim 2, wherein the first end wall or the second end wall, whichever wall body faces the second space, comprises a filter.

4. The flavor source unit as described in claim 1, wherein the lump body side face is fixed to the inner surface of the cylindrical body side wall.

5. The flavor source unit as described in claim 2, wherein the first end wall and the first lump body end face are in contact, and the second space is provided between the second end wall and the second lump body end face.

6. The flavor source unit as described in claim 1, wherein the cylindrical body includes a connect portion which is mechanically connected to a body of a flavor inhaler, and
   wherein the first space is adjacent to the connect portion.

7. The flavor source unit as described in claim 2, wherein the second space has a volume of 5 to 90 percent, inclusive, of a capacity of a space surrounded by the first end wall, the second end wall, and the cylindrical body side wall.

8. The flavor source unit as described in claim 1, wherein the first cylindrical body end face is the same shape and size as the second cylindrical body end face.

9. The flavor source unit as described in claim 1, wherein the first lump body end face is the same shape and size as the second lump body end face.

10. The flavor source unit as described in claim 1, comprising:
    a first end wall which demarcates the inside space of the cylindrical body side wall on a side close to the first cylindrical body end face, and
    a second end wall which demarcates the inside space of the cylindrical body side wall on a side close to the second cylindrical body end face,
    wherein at least either one of the first end wall and the second end wall fills in the first space in such a manner as to contact the columnar lump body.

11. The flavor source unit as described in claim 1, wherein the columnar lump body is a compressed body formed of the plurality of flavor pieces.

12. The flavor source unit as described in claim 1, wherein the plurality of flavor pieces includes at least either an aroma chemical or a binder.

13. The flavor source unit as described in claim 1, wherein a bulk density of the columnar lump body falls in a range from 130 to 160 percent, inclusive, of a loose bulk density of the plurality of flavor pieces.

14. The flavor source unit as described in claim 1, wherein a bulk density of the columnar lump body is higher than a tight bulk density of the plurality of flavor pieces.

15. The flavor source unit as described in claim 1, wherein a compression degree of the plurality of flavor pieces falls in a range from 22 to 34 percent, inclusive.

16. The flavor source unit as described in claim 1, wherein a loose bulk density of the plurality of flavor pieces falls in a range of from 0.40 to 0.54 g/cm$^3$, inclusive.

17. The flavor source unit as described in claim 1, wherein a tight bulk density of the plurality of flavor pieces falls in a range from 0.68 to 0.71 g/cm$^3$, inclusive.

18. The flavor source unit as described in claim 1, wherein each of the plurality of flavor pieces has a size ranging from 0.2 to 1.4 mm, inclusive.

19. A flavor inhaler comprising the flavor source unit as described in claim 1.

20. The flavor inhaler as described in claim 19, comprising a body that holds the flavor source unit in a detachable manner.

21. The flavor inhaler as described in claim 19, comprising an atomization unit located further upstream than the flavor source unit.

22. The flavor inhaler as described in claim 19, wherein the flavor source unit includes a mouthpiece to be held in a user's mouth.

* * * * *